United States Patent [19]

Mai et al.

[11] Patent Number: 4,575,558

[45] Date of Patent: Mar. 11, 1986

[54] PREPARATION OF OPTICALLY ACTIVE 1,3-DIOXOLANE-4-METHANOL COMPOUNDS

[75] Inventors: Khuong H. X. Mai; Ghanshyam Patil, both of Vernon Hills, Ill.

[73] Assignee: American Hospital Supply Corporation, Evanston, Ill.

[21] Appl. No.: 580,492

[22] Filed: Feb. 15, 1984

[51] Int. Cl.[4] .................. C07D 317/00; C07C 59/10; C07C 59/285
[52] U.S. Cl. .................................... 549/453; 562/587
[58] Field of Search .................. 549/453; 562/587

[56] References Cited

U.S. PATENT DOCUMENTS 3,058,981  10/1962  Avakian et al. ............... 549/453

FOREIGN PATENT DOCUMENTS 0158778  9/1982  Japan ........................... 549/453
429096   5/1935  United Kingdom ............. 549/453

OTHER PUBLICATIONS

Lok et al, Chemistry and Physics of Lipids 16 (1976) pp. 115–122.

*Primary Examiner*—Ethel G. Love
*Attorney, Agent, or Firm*—Gildo E. Fato

[57] ABSTRACT

Described is a process for preparing 2,2'-disubstituted-1,3-dioxolane-4-methanol compounds having the formula

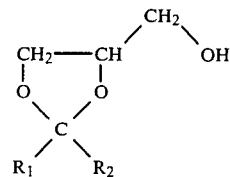

wherein $R_1$ and $R_2$ are each independently hydrogen, alkyl, cycloalkyl or $R_1$ and $R_2$ together with the carbon atom form a 3 to 6 member cycloalkyl group, or aryl, the process comprising: reacting D- or L-serine with a nitrosating agent in an aqueous solution in the presence of formic acid, acetic acid, or propanoic acid to prepare 2,3-dihydroxypropanoic acid (D- or L-glyceric acid), the aqueous solution comprising from about 0.1 to 0.5 liter of water per mole of the serine starting material; reacting the glyceric acid so formed with 2,2-dimethoxypropane in the presence of a loweralkyl alcohol to prepare the D- or L-glyceric acid alkyl ester which is reacted with a selected aldehyde or ketone or the acetal or ketal derivative to prepare the corresponding 1,3-dioxolane derivative. Reacting the 1,3-dioxolane derivative with lithium aluminum hydride provides the desired 2,2'-disubstituted-1,3-dioxolane-4-methanol derivative.

If an alcohol is not used as described above, then the 2,3-dihydroxypropanoic acid is reacted with a selected aldehyde or ketone or the acetal or ketal derivative to prepare the 1,3-dioxolane derivative. The dioxolane derivative is then reacted with lithium aluminum hydride to provide the desired 2,2'-disubstituted-1,3-dioxolane-4-methanol derivative.

The compounds so prepared are intermediates in the preparation of optically active beta-agonists or antagonists.

19 Claims, No Drawings

PREPARATION OF OPTICALLY ACTIVE 1,3-DIOXOLANE-4-METHANOL COMPOUNDS

BACKGROUND OF THE INVENTION

Compounds of the formula

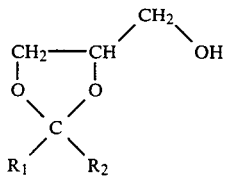

wherein $R_1$ and $R_2$ are each independently hydrogen, alkyl, cycloalkyl or $R_1$ and $R_2$ together with the carbon atom form a 3 to 6 member cycloalkyl group, or aryl are important intermediates in the preparation of beta-agonists and antagonists. The compound L-solketal

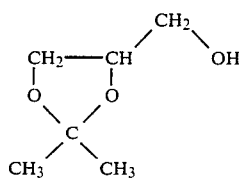

is a particularly important intermediate for preparing optically active beta-agonists and antagonists and a chiral building block in a number of natural products. Lok et al in Chemistry and Physics of Lipids, 16 (1976), 115-122, describes the synthesis of chiral glycerides starting from D- and L-serine and at page 118 describes the preparation of solketal, 2,3-O-isopropylidene-sn-glycerol.

However, the process described requires the use of large amounts of water, an extensive working period of several days, and low processing temperatures. It thus does not lend itself to the large scale production of the noted compounds. In particular, the large quantity of water which is required in relation to the quantity of reactants makes the process inappropriate for large scale production. Furthermore, when attempting to repeat the method of the prior art with the modification of reducing the amount of water by one-half, c.a. 1.5 liters instead of 3 liters of water, it was found that the optical rotation of the final product, solketal, was only $-9.57$ (Neat) instead of $-13.2$ (Neat). This is believed to be due to partial isomerization in higher concentration of hydrochloric acid.

SUMMARY OF THE INVENTION

In accordance with the present invention, disclosed is a process for preparing 2,2'-disubstituted-1,3-dioxolane-4-methanol compounds having the formula

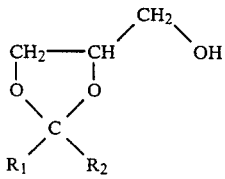

wherein $R_1$ and $R_2$ are each independently hydrogen, alkyl, cycloalkyl or $R_1$ and $R_2$ together with the carbon atom form a 3 to 6 member cycloalkyl group, or aryl, the process comprising:

reacting D- or L-serine with a nitrosating agent such as an alkyl nitrite, nitrosyl halide, nitrosyl sulfuric acid, ammonium nitrite, or a Group Ia or IIa metal nitrite in an aqueous solution in the presence of formic acid, acetic acid, or propanoic acid to prepare 2,3-dihydroxypropanoic acid (D- or L-glyceric acid), the aqueous solution comprising from about 0.1 to 0.5 liter of water per mole of the serine starting material and from about 0.1 to 0.75 liter of acid per mole of serine; reacting the glyceric acid so formed with 2,2-dimethoxypropane, in the presence of a lower alkyl alcohol such as methanol, ethanol, n-propyl or isopropyl alcohol, n-butyl, isobutyl or t-butyl alcohol, pentanol or hexanol, to prepare the D- or L-glyceric acid alkyl ester which is reacted with a selected aldehyde or ketone or the acetal or ketal derivative to prepare the corresponding 1,3-dioxolane derivative. Reacting the 1,3-dioxolane derivative with lithium aluminum hydride provides the desired 2,2'disubstituted-1,3-dioxolane-4-methanol derivative.

If an alcohol is not used as described above, then the 2,3-dihydroxypropanoic acid is reacted with a selected aldehyde or ketone or the acetal or ketal derivative to prepare the 1,3-dioxolane derivative. The dioxolane derivative is then reacted with lithium aluminum hydride to provide the desired 2,2'disubstituted-1,3-dioxolane-4-methanol derivative.

One embodiment of the invention comprises:

reacting D- or L-serine with sodium nitrite in an aqueous solution in the presence of formic acid, acetic acid, or propanoic acid to prepare 2,3-dihydroxypropanoic acid (D- or L-glyceric acid), the aqueous solution comprising from about 0.1 to 0.5 liter of water per mole of the serine starting material and from about 0.1 to 0.75 liter of acid per mole of serine;

reacting the glyceric acid so formed with 2,2-dimethoxypropane in the presence of methanol to prepare the D- or L-glyceric acid methyl ester (methyl D- or L-glycerate);

reacting the glyceric acid methyl ester with 2,2-dimethoxypropane in the presence of an acid to produce methyl 2,3-O-isopropylidene-D- or L-glycerate; and adding a solution of the methyl 2,3-O-isopropylideneglycerate to lithium aluminum hydride to produce the D- or L-solketal, (S)-(+)- or (R)-(−)-2,2-dimethyl-1,3-dioxolane-4-methanol.

Alternatively, the glyceric acid can be reacted with the 2,2-dimethoxypropane without methanol to prepare 2,3-O-isopropylidene D- or L-glyceric acid which is then reacted with lithium aluminum hydride to produce the solketal.

The term "alkyl" as used herein refers to straight or branched chain alkyl radicals containing from 1 to 10 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, or decyl and the like.

The term "cycloalkyl" as used herein refers to cyclic saturated aliphatic radicals containing 3 to 6 carbon atoms in the ring, such as cyclopropyl, cyclobutyl, cyclopentyl or cyclohexyl.

The term "halo" includes chloro, fluoro, bromo and iodo.

The term "aryl" represents phenyl or naphthyl which may be unsubstituted or substituted with loweralkyl of from one to about 6 carbon atoms, halo, hydroxy, or amino.

The term "nitrosating agent" as used herein includes but is not limited to an alkyl nitrite, nitrosyl halide, nitrosyl sulfuric acid, ammonium nitrite or a Group Ia or IIa metal nitrite where the metal is lithium, potassium, sodium, magnesium, barium, calcium or strontium.

DETAILED DESCRIPTION OF THE INVENTION

In accordance with the present invention, disclosed is a process for selectively preparing 2,2'-disubstituted-1,3-dioxolane-4-methanol compounds of the formula

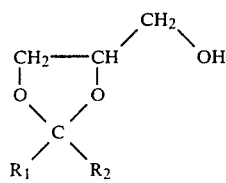

wherein $R_1$ and $R_2$ are each independently hydrogen, alkyl, cycloalkyl or $R_1$ and $R_2$ together with the carbon atom form a 3 to 6 member cycloalkyl group, or aryl, one embodiment of the process comprising:

reacting D- or L-serine with a nitrosating agent such as an alkyl nitrite, nitrosyl halide, nitrosyl sulfuric acid, ammonium nitrite, sodium nitrite or other metal nitrites where the metal is a Group Ia or IIa metal such as lithium, potassium, magnesium, barium, calcium or strontium in an aqueous solution in the presence of formic acid, acetic acid or propanoic acid to prepare 2,3-dihydroxypropanoic acid, the aqueous solution comprising from about 0.1 to 0.5 liter of water per mole of the serine starting material and from about 0.1 to 0.75 liter of acid per mole of serine;

reacting the 2,3-dihydroxypropanoic acid so formed with 2,2-dimethoxypropane, in the presence of a lower alcohol, to prepare the alkyl D- or L-glycerate (D- or L-glyceric acid alkyl ester); reacting the alkyl D- or L-glycerate with 2,2-dimethoxypropane in the presence of an acid to product alkyl 2,3-O-isopropylidene-D- or L-glycerate; adding a solution of the alkyl 2,3-O-isopropylidene-D- or L-glycerate to lithium aluminum hydride to produce the final product, D- or L-solketal, (S)-(+)- or (R)-(−)-2,2-dimethyl-1,3-dioxolane-4-methanol(2,3-O-isopropylidene-D- or L-glycerol).

Alternatively, the 2,3-dihydroxypropanoic acid (D- or L-glyceric acid) is reacted with 2,2-dimethoxypropane without lower alcohol present to prepare 2,3-O-isopropylidene D- or L-glyceric acid which is then reacted with lithium aluminum hydride to produce the solketal.

To prepare other desired derivatives of formula I, the D- or L-glyceric acid alkyl ester prepared as described above is reacted with an appropriate aldehyde or ketone or their acetal or ketal derivative to prepare the 1,3-dioxolane derivative. Reacting the 1,3-dioxolane derivative with lithium aluminum hydride provides the desired 2,2'-disubstituted-1,3-dioxolane-4-methanol derivative.

The following scheme summarizes and is representative of the process of the present invention.

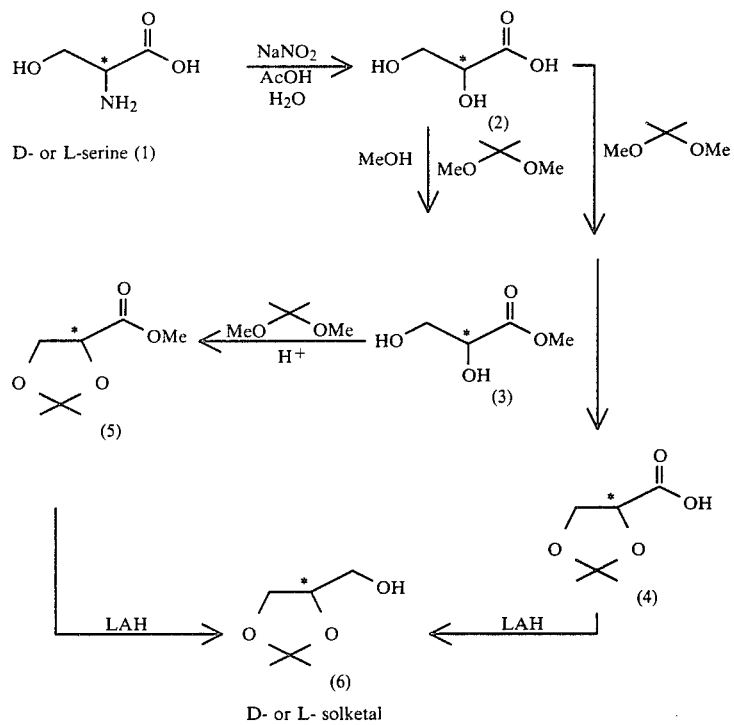

D- or L- solketal

Optically active solketal is an important intermediate in the preparation of optically active beta-agonists or antagonists and a chiral building block for a number of natural products. C. M. Lok et al in Chemistry and Physics of Lipids, 16 (1976) 115–122, describe chiral glyceride synthesis from D- and L-serine and at pages 118 and 119 describe the preparation of solketal, (2,3-O-isopropylidene-D- or L-glycerol) which is also identified as (S)-(+)- or (R)-(−)-2,2-dimethyl-1,3-dioxolane-4-methanol. For convenience hereafter, all reference will be to the L-forms of the compounds. This prior art method has a number of disadvantages, however, primarily the use of large amounts of water, an extensive working period of several days, and low processing temperatures. These requirements make the process inappropriate for large scale production which is necessary for the process to be economically feasible. Specifically, the process requires the use of six liters of water per mole of starting material, L-serine; the initial reaction is conducted at 0° C. for 48 hours and about an additional 24 hours at room temperature. In contrast, the method of the present invention utilizes about one-tenth of the amount of solvent per mole of starting material, from about 0.10 to 0.50 liter of water per mole of L-serine with about 0.30 liter being preferred; the working period is reduced to less than one-half, overnight instead of about three days; and the reaction is carried out at room temperature instead of 0° C. Thus, the process offers a practical method for the large scale preparation of optically active solketal, large scale production being necessary for such a process to be economically feasible.

In the method of the prior art, the L-serine is reacted with sodium nitrite in the presence of hydrochloric acid. In the process described herein, the reaction is carried out in the presence of formic acid, acetic acid, or propanoic acid, with acetic acid being preferred. This modification permits the use of a much reduced amount of solvent, from 6 liters of water per mole of L-serine to about 0.30 liter. This reduction in the quantity of water utilized in the reaction permits the economic preparation of optically active 2,3-dihydroxypropanoic acid, solketal, or other derivatives. Moreover, reducing the amount of water by one-half in the prior art method resulted in an optical rotation of the solketal formed of only $-9.57$ (neat) instead of $-13.2$ (neat), believed due to partial isomerization in higher concentrations of hydrochloric acid.

The method of the present invention can be utilized to make beta-blocking agents such as those described in U.S. Pat. Nos. 4,387,103; 4,402,974; or 4,405,642 for example, or to make the isomers of propranolol, a conventional beta-blocking agent. The L form of propranolol is about twice as potent as the racemic mixture as far as beta-blocking activity is concerned and produces lesser side effects. In addition, D-propranolol is shown to be an effective contraceptive agent. Hence, an economical process for preparing D- or L-propranolol is highly desirable. Likewise, the method can be used to make other beta-blocking agents such as metoprolol, timolol, pindolol, practolol, or carteolol.

In the following examples, Example I describes the preparation of L-solketal without the use of methanol in the second step of the procedure, the conversion of 2,3-dihydroxypropanoic acid (L-glyceric acid). In this embodiment of the invention, the 2,3-dihydroxypropanoic acid is reacted with 2,2-dimethoxypropane to prepare 2,3-O-isopropylidene-L-glyceric acid which is then reacted with lithium aluminum hydride to prepare the L-solketal.

In Example II, the 2,3-dihydroxypropanoic acid is reacted with 2,2-dimethoxypropane and methanol to prepare methyl-L-glycerate (L-glyceric acid methyl ester) which is then reacted with 2,2-dimethoxypropane to produce methyl-2,3-O-isopropylidene-L-glycerate. This in turn is reacted with lithium aluminum hydride to prepare L-solketal, 2,3-O-isopriopylidene-L-glycerol[(R)-(−)-2,2-dimethyl-1,3-dioxolane-4-methanol].

In order to illustrate the manner in which the above compounds may be prepared, reference is made to the following examples, which, however, are not meant to limit or restrict the scope of the invention in any respect.

EXAMPLE I

In a 6 liter (L) flask was placed 630 g (6 moles) of L-serine (1), 1.8 L of water and 2.4 L of acetic acid. The flask was surrounded with ice and the internal temperature was maintained below $+20°$ C. Sodium nitrite (500 g, 7.2 moles) was added, with stirring, at a rate of 20 g every 15 minutes. (An aqueous solution of sodium nitrite could also be used by adding dropwise to the reaction mixture.) When this addition was complete, the solution was warmed to room temperature (23°–26° C.) and stirred overnight (16–20 hours).

Concentrated hydrochloric acid (650 mL, 7.8 equiv.) was added in one lot. The solution was then transferred equally into four 3 L round-bottomed flasks and evaporated in vacuo at 75° C. until the solvent ceased to collect. The residue contained crystalline sodium chloride, crude 2,3-dihydroxypropanoic acid (2), water, and acetic acid. The slurries were filtered and the flasks were rinsed with a small amount of acetone. The filtrates were combined and evaporated to near dryness. To the filtrates, 1 L of toluene was added and evaporated to azeotrope trace of water. This operation was repeated twice. The residue was then taken up with 1.5 L of acetone and 1.8 L (1.5 Kg) of 2,2-dimethoxypropane and filtered to remove most of sodium chloride. The filtrate was then stirred overnight at room temperature (r.t.).

Evaporation of the above solution gave an oil, 2,3-O-isopropylidene-L-glyceric acid (4), which was treated with 1 L of toluene and evaporated in vacuo at 65° C. In the meantime, a reducing solution was prepared as follows.

In a 3 neck-12 L round-bottomed flask equipped with a mechanical stirrer, an adding funnel and a condenser, was placed 250 g (6.6 moles) of lithium aluminum hydride. Eight liters of tetrahydrofuran was slowly added with stirring. The flask was then surrounded with ice. To this slurry the above crude oil (about 800 g) was added in a slow stream maintaining a constant reflux. After about three-fourths of the material was added, the ice-bath was removed and addition was continued. Th funnel was rinsed several times with a small amount of tetrahydrofuran. Stirring was continued for another hour. Again, the flask was surrounded with ice and excess lithium aluminum hydride was destroyed by successive addition of 250 mL of water, 250 mL of 15% sodium hydroxide, and another 250 mL of water. After stirring for 30 minutes, the slurry was filtered, washed with 1 L of tetrahydrofuran and the filtrate was evaporated to an oil which was treated with 1 L of toluene and evaporated in vacuo. The resulting yellow oil (about 300 g) was transferred to a 500 mL round-bottomed flask and distilled under reduced pressure. After removing most of the toluene (about 20 mL, b.p. 30°–60° C., 2–5 mm), the temperature was raised to 60°–80° C. and about 220 g (29%) of L-solketal (6) was collected, b.p. 75° C., 2 mm, n. 1.4337, $\alpha_D^{25} -13.234$ (neat), TLC Rf 0.57 (toluene-acetone, 7:3); NMR and IR were consistent with the assigned structure [Lit. b.p. 75° C., 10 mm; n 1.4345; $\alpha_D^{25} = -13.2$ (neat)].

A third higher b.p. fraction 10 g; 80° C., 0.5 mm) was also collected; TLC showed a mixture of product and impurities. Only a small amount of water-soluble black residue (about 20 g) was left in the flask.

EXAMPLE II

In a 6 L flask was placed 630 g (6 moles) of L-serine (1), 1.8 L of water and 2.4 L of acetic acid. The flask was surrounded with ice and the internal temperature was maintained below 20° C. Sodium nitrite (500 g, 7.2 moles) was added, with stirring at a rate of 20 g every 15 min. When this addition was complete, the solution was warmed to r.t. (23°-26° C.) and stirred overnight. (16-20 h.)

Concentrated hydrochloric acid (650 mL, 7.8 equiv.) was added in one lot. The solution was then transferred equally into four 3 L round-bottomed flasks and evaporated in vacuo at 75° C. until the solvent ceased to collect. The residue contained crystalline sodium chloride, crude 2,3-dihydroxypropanoic acid (2), water, and acetic acid. The slurries were filtered and the flasks were rinsed with a small amount of acetone. The filtrates were combined and evaporated to near dryness. The residue was co-evaporated with 1 L of toluene to azeotrope traces of water. This operation was repeated twice. The residue was then taken up with 1.5 L of methanol and 1.2 L of 2,2-dimethoxypropane, added dropwise with 150 mL of SOCl₂, stirred for 2 hours, filtered, and the filtrate was evaporated to an oil. The oily residue, L-glyceric acid methyl ester (3), was then mixed with 1.5 L of acetone and 1.8 L (1.5 Kg.) of 2,2-dimethoxypropane and the mixture was filtered. The filtrate was then stirred overnight at room temperature.

Evaporation of the above solution gave an oil, methyl 2,3-O-isopropylidene-L-glycerate (5), which was treated with 1 L of toluene and evaporated in vacuo at 65°. In the meantime, a reducing solution was prepared as follows.

In a 3 neck-12 L round-bottomed flask equipped with a mechanical stirrer, an adding funnel, and a condenser was placed 250 g (6.6 moles) of lithium aluminum hydride. Eight liters of tetrahydrofuran was slowly added with stirring. The flask was then surrounded with ice. To this slurry the above crude oil (about 800 g) was added at a slow stream maintaining a constant reflux. Stirring was continued for another hour. Excess lithium aluminum hydride was destroyed by successive addition of 250 mL of water, 250 mL of 15% sodium hydroxide, and another 250 mL of water. After stirring for 30 minutes, the slurry was filtered, washed with 1 L of tetrahydrofuran, and the filtrate was evaporated to an oil which was treated with 1 L of toluene and evaporated in vacuo. The resulting yellow oil, (about 300 g.), was transferred to a 500 mL round-bottomed flask and distilled under reduced pressure. After removing most of the toluene (about 40 ML, b.p. 30°-60° C., 2-5 mm), the temperature was raised to 60°-80° C. and about 360 g (45%) of L-solketal was collected, b.p. 75° C., 2 mm, n. 1.4337, $\alpha_D{}^{25}$ −13.234 (neat), TLC Rf 0.57 (toluene-acetone, 7:3) NMR and IR were consistent with the assigned structure [Lit. b.p. 75°, 10 mm; n 1.4345; $\alpha_D{}^{25}$ = −13.2 (neat)].

A third higher b.p. fraction 10 g; 80° C., 0.5 mm) was also collected; TLC showed a mixture of product and impurities. Only a small amount of water-soluble black residue (about 20 g) was left in the flask.

EXAMPLE III

Using the method of Example II, 14 kilograms of L-solketal (2,3-O-isopropylidene-L-glycerol) (6) were prepared using the following amounts of reactants and solvents:
STEP 1:
  20 kilograms (kg) L-serine (1)
  57 liters (L) deionized water
  79.5 kg. acetic acid
  15.9 kg. sodium nitrite
  19 L hydrochloric acid
STEP 2:
  12.5 gallons (gal) methanol
  10 gal dimethoxypropane
  4.8 kg. thionyl chloride
STEP 3:
  12.5 gal acetone
  15 gal dimethoxypropane
YIELD: 24.5 kg. oil
STEP 4: Reduction, completed in two portions
EACH REACTION:
  160 L tetrahydrofuran
  3 kg lithium aluminum hydride
  3 L water
  3 L 15% sodium hydroxide
  3 L water
TOTAL YIELD: 14 Kg, $\alpha_D{}^{25}$ −13.60 (neat)

EXAMPLE IV

Using the method of Example II and starting with 200 g of D-serine, 114 g D-solketal were prepared, $\alpha_D{}^{25}$ +13.56 (neat), bp 55°-75° C., 0.6 mm Hg.

EXAMPLE V

Using the method of Example II but reacting the L-glyceric acid methyl ester (3) with 1,1-dimethoxy cyclohexane, 2,2'-cyclohexylidene-1,3-dioxolane-4-methanol is prepared according to the following reaction scheme:

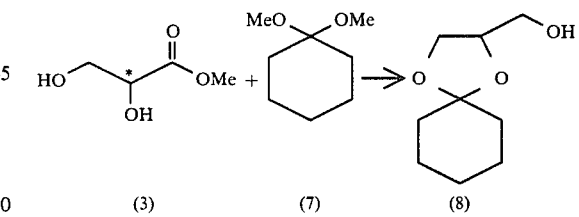

EXAMPLE VI

By using the method of Example I, namely without methanol, and reacting the 2,3-dihydroxypropanoic acid (2) with the 1,1-dimethoxy cyclohexane (7), the 2,2'cyclohexylidene-1,3-dioxolane (8) of Example V can be prepared.

What is claimed is:

1. A process for the preparation of 2,3-dihydroxypropanoic acid which comprises reacting L-serine with a nitrosating agent in an aqueous solution in the presence of formic acid, acetic acid, or propanoic acid at about room temperature for a period of about 8 to 20 hours and wherein said aqueous solution of L-serine comprises from 0.10 to 0.5 liter of water per mole of L-serine and said acid is present in an amount of from 0.1 to 0.75 liter per mole of L-serine.

2. The process of claim 1 wherein the L-serine is reacted with ammonium nitrite, an alkyl nitrite, nitrosyl halide, nitrosyl sulfuric acid, or a Group Ia or IIa metal nitrite.

3. The process of claim 2 wherein the L-serine is reacted with sodium nitrite or potassium nitrite in the presence of acetic acid.

4. The process of claim 3 wherein the L-serine is reacted with sodium nitrite.

5. A process for preparing a selected 2,2'-disubstituted-1,3-dioxolane-4-methanol derivative having the formula

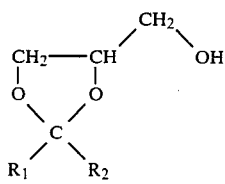

wherein $R_1$ and $R_2$ are each independently hydrogen, alkyl, cycloalkyl or $R_1$ and $R_2$ together with the carbon atom form a 3 to 6 member cycloalkyl group, or aryl, the process comprising:
  reacting D- or L-serine with a nitrosating agent in an aqueous solution in the presence of acetic acid, formic acid, or propanoic acid at about room temperature for a period of about 8 to 20 hours and wherein said aqueous solution of D- or L-serine comprises from about 0.10 to 0.5 liter of water per mole of D- or L-serine and said acid is present in an amount of from about 0.1 to 0.75 liter per mole of D- or L-serine to produce 2,3-dihydroxypropanoic acid;
  adding to the 2,3-dihydroxypropanoic acid so produced 2,2-dimethoxypropane in the presence of a loweralkyl alcohol to produce D- or L-glyceric acid alkyl ester;
  reacting the D- or L-glyceric acid alkyl ester with an appropriate aldehyde, ketone or their acetal or ketal derivative to produce the corresponding 1,3-dioxolane derivative; and
  reacting the 1,3-dioxolane derivative so produced with lithium aluminum hydride to produce the desired 2,2'-disubstituted-1,3-dioxolane-4-methanol derivative.

6. The process of claim 5 wherein the D- or L-serine is reacted with ammonium nitrite, an alkyl nitrite, nitrosyl halide, nitrosyl sulfuric acid or a Group Ia or IIa metal nitrite.

7. The process of claim 6 wherein the D- or L-serine is reacted with ammonium nitrite, sodium nitrite or potassium nitrite in the presence of formic acid or acetic acid, and the loweralkyl alcohol is methanol, ethanol or propanol.

8. The process of claim 7 wherein the D- or L-serine is reacted with sodium nitrite in the presence of acetic acid and the loweralkyl alcohol is methanol.

9. The process of claim 5 wherein the 2,3-dihydroxypropanoic is reacted with an appropriate aldehyde, ketone or their acetal or ketal derivative to produce 2,3-O-isopropylidene D- or L-glyceric acid which is then reacted with lithium aluminum hydride to produce the desired 2,2'-disubstituted-1,3-dioxolane-4-methanol derivative.

10. The process of claim 9 wherein the D- or L-serine is reacted with ammonium nitrite, sodium nitrite or potassium nitrite in the presence of formic acid or acetic acid.

11. The process of claim 10 wherein the D- or L-serine is reacted with sodium nitrite in the presence of acetic acid.

12. A process for the preparation of L-solketal which comprises reacting L-serine with a nitrosating agent in an aqueous solution in the presence of acetic acid, formic acid, or propanoic acid at about room temperature for a period of about 8 to 20 hours and wherein said aqueous solution of L-serine comprises from about 0.10 to 0.5 liter of water per mole of L-serine and said acid is present in an amount of from about 0.1 to 0.75 liter per mole of L-serine to produce 2,3-dihydroxypropanoic acid;
  adding to the 2,3-dihydroxypropanoic acid so produced 2,2-dimethoxypropane in the presence of a lower alcohol to produce L-glyceric acid alkyl ester;
  reacting the L-glyceric acid alkyl ester with 2,2-dimethoxypropane to produce methyl 2,3-O-isopropylidene-L-glycerate; and
  reacting the methyl 2 3-O-isopropylidene-L-glycerate so produced with lithium aluminum hydride to produce L-solketal.

13. The process of claim 12 wherein the L-serine is reacted with ammonium nitrate, an alkyl nitrite, nitrosyl halide, nitrosyl sulfuric acid, or a Group Ia or IIa metal nitrite.

14. The process of claim 13 wherein the L-serine is reacted with ammonium nitrite, sodium nitrite or potassium nitrite in the presence of formic acid or acetic acid and the loweralkyl alcohol is methanol, ethanol or propanol.

15. The process of claim 14 wherein the L-serine is reacted with sodium nitrite in the presence of acetic acid and the loweralkyl alcohol is methanol, to produce L-glyceric acid methyl ester.

16. The process of claim 12 wherein the 2,3-dihydroxypropanoic acid so produced is reacted with 2,2-dimethoxypropane to prepare 2,3-O-isopropylidene-L-glyceric acid which in turn is reacted with lithium aluminum hydride to produce L-solketal.

17. The process of claim 16 wherein the L-serine is reacted with ammonium nitrite, sodium nitrite or potassium nitrite in the presence of formic acid or acetic acid.

18. The process of claim 17 wherein the L-serine is reacted with sodium nitrite in the presence of acetic acid.

19. A process for preparing a selected 2,2'-disubstituted-1,3-dioxolane-4-methanol derivative having the formula

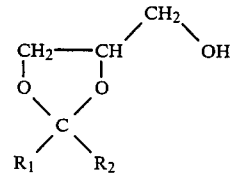

wherein $R_1$ and $R_2$ are each independently hydrogen, alkyl, cycloalkyl or $R_1$ and $R_2$ together with the carbon atom form a 3 to 6 member cycloalkyl group, or aryl, the process comprising: reacting D- or L-serine with a nitrosating agent in an aqueous solution in the presence of acetic acid, formic acid, or propanoic acid at about room temperature for a period of about 8 to 20 hours and wherein said aqueous solution of D- or L-serine comprises from about 0.10 to 0.5 liter of water per mole of D- or L-serine and said acid is present in an amount of from about 0.1 to 0.75 liter per mole of D- or L-serine to produce 2,3-dihydroxypropanoic acid; adding to the 2,3-dihydroxypropanoic acid so produced 2,2-dimethoxypropane to produce the corresponding 1,3-dioxolane derivative; and reacting the 1,3-dioxolane derivative so produced with lithium aluminum hydride to produce the desired 2,2'-disubstituted-1,3-dioxolane-4-methanol derivative.

* * * * *